US008229545B2

(12) United States Patent
Afonso

(10) Patent No.: US 8,229,545 B2
(45) Date of Patent: Jul. 24, 2012

(54) SYSTEM AND METHOD FOR MAPPING COMPLEX FRACTIONATED ELECTROGRAM INFORMATION

(75) Inventor: Valtino Afonso, Oakdale, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 586 days.

(21) Appl. No.: 11/647,301

(22) Filed: Dec. 29, 2006

(65) Prior Publication Data

US 2007/0208260 A1    Sep. 6, 2007

Related U.S. Application Data

(63) Continuation-in-part of application No. 11/227,006, filed on Sep. 15, 2005, now Pat. No. 8,038,625.

(60) Provisional application No. 60/800,852, filed on May 17, 2006.

(51) Int. Cl.
*A61N 5/05* (2006.01)
*A61N 5/02* (2006.01)
*A61N 1/00* (2006.01)

(52) U.S. Cl. ............. 600/424; 600/506; 600/507; 607/2

(58) Field of Classification Search .................. 600/424, 600/506–507
See application file for complete search history.

(56) References Cited

U.S. PATENT DOCUMENTS

| 4,721,114 A | 1/1988 | Dufault et al. |
| 5,058,599 A | 10/1991 | Andersen |
| 5,662,108 A | 9/1997 | Budd et al. |
| 5,697,377 A | 12/1997 | Wittkampf |
| 5,954,665 A * | 9/1999 | Ben-Haim .................... 600/515 |
| 5,983,126 A | 11/1999 | Wittkampf |
| 6,236,883 B1 * | 5/2001 | Ciaccio et al. ................ 600/515 |
| 6,625,482 B1 | 9/2003 | Panescu et al. |

(Continued)

FOREIGN PATENT DOCUMENTS

WO    WO-2007035306    3/2007

OTHER PUBLICATIONS

Koonlawee et al., A New Approach for Catheter Ablation of Atrial Fibrillation: Mapping of the Electrophysiologic Substrate, Dec. 2003, Journal of American College of Cardiology, vol. 43, No. 11, pp. 2044-2053.*

(Continued)

*Primary Examiner* — Nicole F Lavert
(74) *Attorney, Agent, or Firm* — Wiley Rein LLP

(57) ABSTRACT

A system for presenting information representative of patient electrophysiological activity, such as complex fractionated electrogram information, includes at least one electrode to measure electrogram information from the heart surface, at least one processor coupled to the at least one electrode to receive the electrogram information and measure a location of the at least one electrode within the heart, and a presentation device to present the electrogram information as associated with the location at which it was measured on a model of the patient's heart. A memory may also be provided in which to store the associated electrogram information and measured location. Data may be analyzed using both time-domain and frequency-domain information to create a three-dimensional map. The map displays the data as colors, shades of color, and/or grayscales, and may further utilize contour lines, such as isochrones, to present the information.

13 Claims, 11 Drawing Sheets

U.S. PATENT DOCUMENTS

| | | |
|---|---|---|
| 6,658,279 B2 | 12/2003 | Swanson et al. |
| 7,076,300 B1 | 7/2006 | Kroll et al. |
| 2004/0059237 A1 | 3/2004 | Narayan et al. |
| 2004/0254437 A1 | 12/2004 | Hauck et al. |
| 2005/0203394 A1 | 9/2005 | Hauck |

OTHER PUBLICATIONS

Koonlawee et al., A New Approach for Catheter Ablation of Atrial Fibrillation: Mappling of the Electrophysiologic Substrate, Jun. 2004, Journal of the American College of Cardiology, vol. 43, No. 11 2004, pp. 2044-2053.*

PCT International Search Report and Written Opinion of the International Searching Authority for PCT/US07/69055 dated Apr. 7, 2008.

Markides, Vias et al., "New Mapping Technologies: An Overview with a Clinical Perspective", *Journal of Interventional Cardiac Electrophysiology* 13 2005, 43-51.

Sanders, Prashanthan et al., "Spectral Analysis Identifies Sites of High-Frequency Activity Maintaining Atrial Fibrillation in Humans", *Circulation* Aug. 9, 2005 , 789-797.

Extended European Search Report on PCT/US2006035290 (May 7, 2010).

Koonlawee Nademanee, MD et al., "How to perform electrogram-guided atrial fibrillation ablation," 3 Heart Rhythm 981 (2006).

Ross J. Hunter et al., "Validation of a Classification System to Grade Fractionation in Atrial Fibrillation and Correlation with Automated Detection Systems," 11 Europace 1587 (2009).

Pachon, Jose, C., et. al., "Cardioneuroablation"—new treatment for neurocardiogenic syncope, functional AV block and sinus dysfunction using catheter RF-ablation, Europace, (2005) 7, 1-13, The European Society of Cardiology.

Pachon, Jose, C., et. al., A new treatment for atrial fibrillation based on spectral analysis to guide the catheter RF-ablation, Europace, (2004) 6, 590-601, The European Society of Cardiology.

Nademanee, Koonlawee, M.D., FACC, et. al., A new approach for catheter ablation of atrial fibrillation: Mapping of the electrophysiologic substrate, Journal of the American College of Cardiology, (2004) vol. 43, No. 11, 2044-2053.

Barber, C.B., et. al., The Quickhull algorithm for convex hulls, ACM Trans. On Mathematical Software, 22(4):469-483 Dec. 1996.

Extended European Search Report issued in European Application No. 10181954.8, dated Jan. 10, 2011.

Nademanee, et al., A New Approach for Catheter Ablation of Atrial Fibrillation: Mapping of the Electrophysiologic Substrate, Journal of the American College of Cardiology, pp. 2044-2053, vol. 43, No. 11, 2004.

* cited by examiner

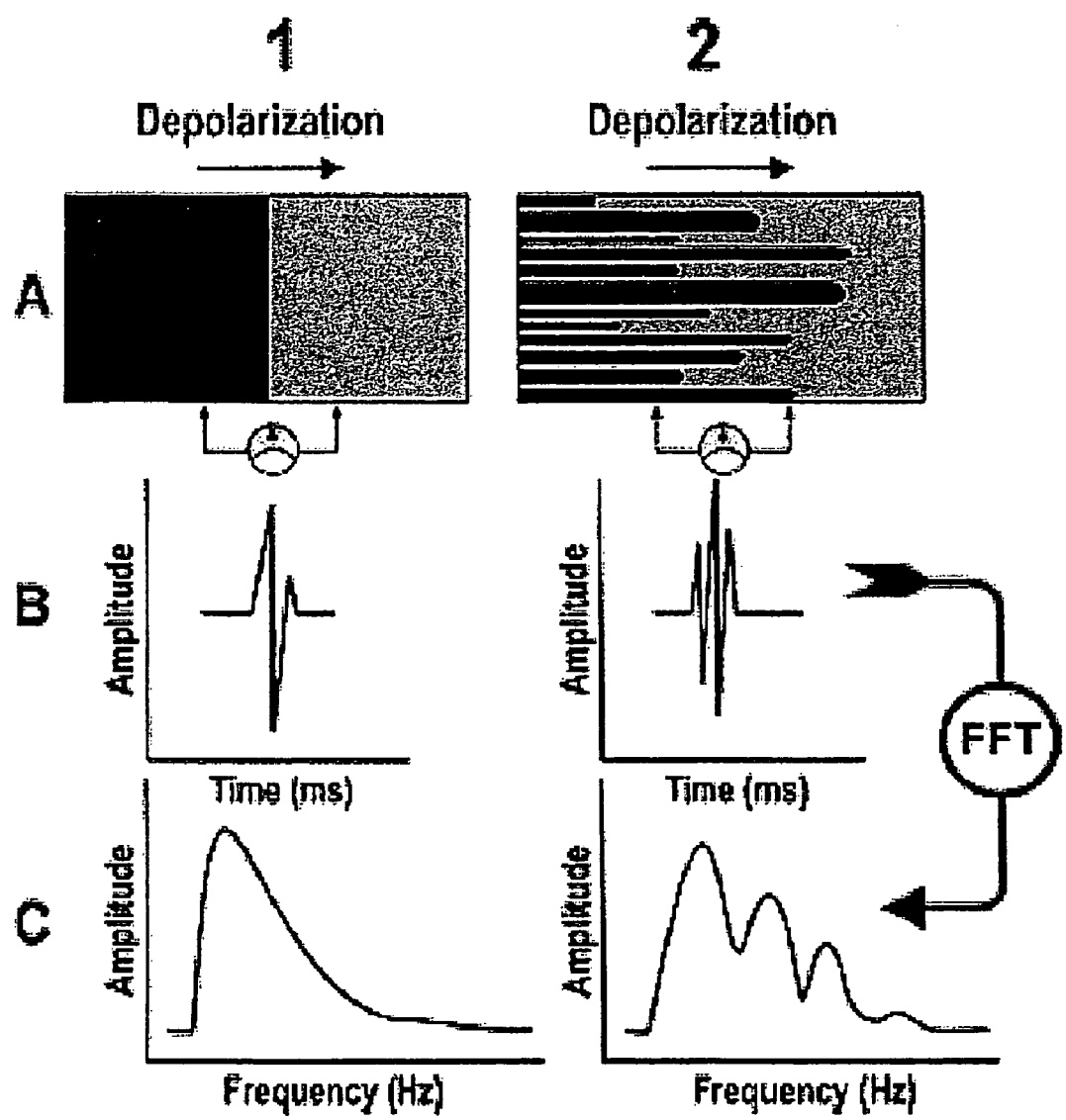
Prior Art  FIG. 8

SYSTEM AND METHOD FOR MAPPING COMPLEX FRACTIONATED ELECTROGRAM INFORMATION

CROSS-REFERENCE TO RELATED APPLICATIONS

This application is a continuation-in-part of U.S. application Ser. No. 11/227,006, filed 15 Sep. 2005, now U.S. Pat. No. 8,038,625, issued on 28 Sep. 2011, which is hereby expressly incorporated by reference as though fully set forth herein.

This application claims the benefit of U.S. provisional application No. 60/800,852, filed 17 May 2006, which is hereby expressly incorporated by reference as though fully set forth herein.

BACKGROUND OF THE INVENTION a. Field of the Invention

The instant invention relates to an electrophysiology apparatus used to measure electrical activity occurring in a heart of a patient and to visualize the electrical activity and/or information related to the electrical activity. In particular, the instant invention relates to three-dimensional mapping of the electrical activity associated with complex fractionated electrograms and/or the information related to the complex fractionated electrograms.

b. Description of the Prior Art

The heart contains two specialized types of cardiac muscle cells. The majority, around ninety-nine percent, of the cardiac muscle cells is contractile cells, which are responsible for the mechanical work of pumping the heart. Autorhythmic cells comprise the second type of cardiac muscle cells, which function as part of the autonomic nervous system to initiate and conduct action potentials responsible for the contraction of the contractile cells. The cardiac muscle displays a pacemaker activity, in which membranes of cardiac muscle cells slowly depolarize between action potentials until a threshold is reached, at which time the membranes fire or produce an action potential. This contrasts with a nerve or skeletal muscle cell, which displays a membrane that remains at a constant resting potential unless stimulated. The action potentials, generated by the autorhythmic cardiac muscle cells, spread throughout the heart triggering rhythmic beating without any nervous stimulation.

The specialized autorhythmic cells of cardiac muscle comprising the conduction system serve two main functions. First, they generate periodic impulses that cause rhythmical contraction of the heart muscle. Second, they conduct the periodic impulses rapidly throughout the heart. When this system works properly, the atria contract about one sixth of a second ahead of ventricular contraction. This allows extra filling of the ventricles before they pump the blood through the lungs and vasculature. The system also allows all portions of the ventricles to contract almost simultaneously. This is essential for effective pressure generation in the ventricular chambers. The rates at which these autorhythmical cells generate action potentials differ due to differences in their rates of slow depolarization to threshold in order to assure the rhythmical beating of the heart.

Normal autorhythmic cardiac function may be altered by neural activation. The medulla, located in the brainstem above the spinal cord, receives sensory input from different systemic and central receptors (e.g., baroreceptors and chemoreceptors) as well as signals from other brain regions (e.g., the hypothalamus). Autonomic outflow from the brainstem is divided principally into sympathetic and parasympathetic (vagal) branches. Efferent fibers of these autonomic nerves travel to the heart and blood vessels where they modulate the activity of these target organs. The heart is innervated by sympathetic and vagal fibers. Sympathetic efferent nerves are present throughout the atria (especially in the sinoatrial node) and ventricles, including the conduction system of the heart. The right vagus nerve primarily innervates the sinoatrial node, whereas the left vagus nerve innervates the atrial-ventricular node; however, there can be significant overlap in the anatomical distribution. Efferent vagal nerves also innervate atrial muscle. However, efferent vagal nerves only sparsely innervate the ventricular myocardium. Sympathetic stimulation increases heart rate and conduction velocity, whereas parasympathetic (vagal) stimulation of the heart has opposite effects.

An arrhythmia occurs when the cardiac rhythm becomes irregular, i.e., too fast (tachycardia) or too slow (bradycardia), or the frequency of the atrial and ventricular beats are different. Arrhythmias can develop from either altered impulse formation or altered impulse conduction. The former concerns changes in rhythm that are caused by changes in the pacemaker cells resulting in irregularity or by abnormal generation of action potentials by sites other than the sinoatrial node, i.e., ectopic foci. Altered impulse conduction is usually associated with complete or partial blockage of electrical conduction within the heart. Altered impulse conduction commonly results in reentry, which can lead to tachyarrhythmias. Reentry can take place within a small local region or it can occur, for example, between the atria and ventricles (global reentry). Reentry requires the presence of a unidirectional block within a conducting pathway usually caused by partial depolarization of the pacemaker cells. Arrhythmias can be either benign or more serious in nature depending on the hemodynamic consequences of arrhythmias and their potential for changing into lethal arrhythmias.

Electrophysiology studies may be used to identify and treat these arrhythmias. In one exemplary system, a measurement system introduces a modulated electric field into the heart chamber. The blood volume and the moving heart wall surface modify the applied electric field. Electrode sites within the heart chamber passively monitor the modifications to the field and a dynamic representation of the location of the interior wall of the heart is developed for display to the physician. Electrophysiology signals generated by the heart itself are also measured at electrode sites within the heart and these signals are low pass filtered and displayed along with the dynamic wall representation. This composite dynamic electrophysiology map may be displayed and used to diagnose the underlying arrhythmia.

In addition to mapping for diagnosis, the measurement system can also be used to physically locate a therapy catheter in a heart chamber. A modulated electrical field delivered to an electrode on this therapy catheter can be used to show the location of the therapy catheter within the heart. The therapy catheter location can be displayed on the dynamic electrophysiology map in real time along with the other diagnostic information. Thus the therapy catheter location can be displayed along with the intrinsic or provoked electrical activity of the heart to show the relative position of the therapy catheter tip to the electrical activity originating within the heart itself. Consequently, the physician can guide the therapy catheter to any desired location within the heart with reference to the dynamic electrophysiology map.

The dynamic electrophysiology map is generally produced in a step-wise process. First, the interior shape of the heart is determined. This information is derived from a sequence of geometric measurements related to the modulation of the applied electric field. Knowledge of the dynamic shape of the heart is used to generate a representation of the interior surface of the heart. Next, the intrinsic electrical activity of the heart is measured. The signals of physiologic origin are passively detected and processed such that the magnitude of the potentials on the wall surface may be displayed on the wall surface representation. The measured electrical activity is displayed on the wall surface representation in any of a variety of formats, for example, in various colors or shades of a color. Finally, a location current may be delivered to a therapy catheter within the same chamber. The potential sensed from this current may be processed to determine the relative or absolute location of the therapy catheter within the chamber. These various processes occur sequentially or simultaneously several hundred times a second to give a continuous image of heart activity and the location of the therapy device.

One exemplary system for determining the position or location of a catheter in the heart is described in U.S. Pat. Nos. 5,697,377 (the '377 patent) and 5,983,126 (the '126 patent) to Wittkampf. The '377 patent and the '126 patent are hereby incorporated herein by reference in their entirety. In the Wittkampf system, current pulses are applied to orthogonally placed patch electrodes placed on the surface of the patient. These surface electrodes are used to create axis specific electric fields within the patient. The Wittkampf references teach the delivery of small amplitude, low current pulses supplied continuously at three different frequencies, one on each axis. Any measurement electrode placed in these electric fields (for example within the heart) measures a voltage that varies depending on the location of the measurement electrode between the various surface electrodes on each axis. The voltage across the measurement electrode in the electric field in reference to a stable positional reference electrode indicates the position of the measurement electrode in the heart with respect to that reference. Measurement of the difference in voltage over the three separate axes gives rise to positional information for the measurement electrode in three dimensions.

BRIEF SUMMARY OF THE INVENTION

The present invention expands the previous capabilities of cardiac electrophysiology mapping systems to provide additional diagnostic data using both the time-domain and frequency-domain representations of electrophysiology data. A three-dimensional map of the electrical activity and/or the information related to the electrical activity is created. Exemplary maps include a time difference between action potentials at a roving electrode and a reference electrode, the peak-to-peak voltage of action potentials at the roving electrode, the peak negative voltage of action potentials at the roving electrode, complex fractionated electrogram information, a dominant frequency of an electrogram signal, a maximum peak amplitude at the dominant frequency, a ratio of energy in one band of the frequency-domain to the energy in a second band of the frequency-domain, a low-frequency or high-frequency passband of interest, a frequency with the maximum energy in a passband, a number of peaks within a passband, an energy, power, and/or area in each peak, a ratio of energy and/or area in each peak to that in another passband, and a width of each peak in a spectrum. Colors, shades of color, and/or grayscales are assigned to values of the parameters and colors, shades of colors, and/or grayscales corresponding to the parameters for the electrograms sampled by the electrodes are updated on the three-dimensional model. Maps may be presented by utilizing contour lines, such as isochrones.

According to a first embodiment of the invention, a system for presenting information representative of electrophysiological activity of a patient includes: at least one electrode adapted to receive at least one stream of electrical data from at least one location within a heart of a patient, the data including complex fractionated electrogram information; at least one processor coupled to the at least one electrode to receive the at least one stream of electrical data from at least one location and to determine the measurement location of the electrode within the heart of the patient while it is receiving the stream of electrical data, the at least one processor associating the measurement location with the at least one stream of electrical data being received; at least one memory to store the measurement location of the electrode and the at least one stream of electrical data being received; software to analyze the at least one stream of electrical data to identify occurrences of discrete electrical activations within a predetermined window and to quantify the complex fractionated electrogram information contained in the predetermined window; and a presentation device to present the quantified complex fractionated electrogram information and its respective measurement location on a model of the heart of the patient. The software may quantify the standard deviation, the mean, or both the standard deviation and the mean of the time intervals between occurrences of discrete electrical activations, which may then be presented on the model at a location corresponding to a point at which the electrical data was measured. The system may optionally employ a plurality of electrodes simultaneously receiving electrical data from a plurality of locations within the patient.

According to another aspect of the invention, a method of analyzing and presenting information representative of electrophysiological information of a patient includes the steps of: obtaining a cardiac electrophysiology map including position information identifying a plurality of measurement locations and electrophysiology measurements made at each of the plurality of measurement locations, the electrophysiology measurements including at least one stream of complex fractionated electrogram information; processing the at least one stream of complex fractionated electrogram information measured at one of the plurality of measurement locations to identify occurrences of discrete electrical activations within a predetermined window and to quantify the complex fractionated electrogram information contained in the predetermined window; and presenting the quantified complex fractionated electrogram information and its respective measurement location on a model of the heart of the patient. The method optionally employs a plurality of electrodes simultaneously receiving electrical data from a plurality of measurement locations within the patient, which may be processed, quantified, and presented on the model. The complex fractionated electrogram information may be presented on the model as colors, shades of colors, or a grayscale.

In yet another aspect of the present invention, a method of analyzing and presenting information representative of electrophysiological activity of a patient includes the steps of: obtaining a cardiac electrophysiology map including position information identifying a measurement location and electrophysiology measurements made at the measurement locations, the electrophysiology measurements including at least one stream of complex fractionated electrogram information; processing the at least one stream of complex fractionated electrogram information measured at the measurement locations to identify occurrences of discrete electrical activations within a predetermined window and to quantify the standard deviation of the time intervals between occurrences of discrete electrical activations within the predetermined window;

and presenting the standard deviation information on the model of the heart at a location corresponding to a point where the at least one stream of complex fractionated electrogram information was measured.

In still another embodiment, a system for presenting information representative of electrophysiological activity of a patient includes: at least one electrode adapted to measure electrogram information from a surface of a heart of a patient; at least one processor coupled to the at least one electrode to receive the electrogram information and to measure a location of the at least one electrode within the heart of the patient at which the electrogram information is measured, wherein the at least one processor associates the measured location of the at least one electrode with the received electrogram information; and a presentation device to present the associated electrogram information and measured location on a model of the heart of the patient. The electrogram information optionally includes complex fractionated electrogram information. A memory may also be provided in which to store the associated electrogram information and measured location.

According to a further aspect of the invention, a method of presenting information representative of patient electrophysiological characteristics on a model of a surface of a heart includes the steps of: a) introducing at least one electrode into the heart; b) measuring electrogram information from the surface of the heart via the at least one electrode; c) measuring location information of the at least one electrode; d) deriving, from the measured location information, location information for a point on the surface of the heart at which the electrogram information is measured; e) associated the derived location information and measured electrogram information; and f) presenting information indicative of the associated location information and electrogram information on the model of the surface of the heart. Steps b) through f) may be repeated a plurality of times as the electrode moves within the heart. Alternatively, steps b) through f) may be repeated for a plurality of electrodes introduced into the heart.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 8 shows side-by-side comparisons of electrograms for typical compact and fibrillar myocardial muscle tissues in the time-domain and frequency-domain.

DETAILED DESCRIPTION OF THE INVENTION

Figure 1:
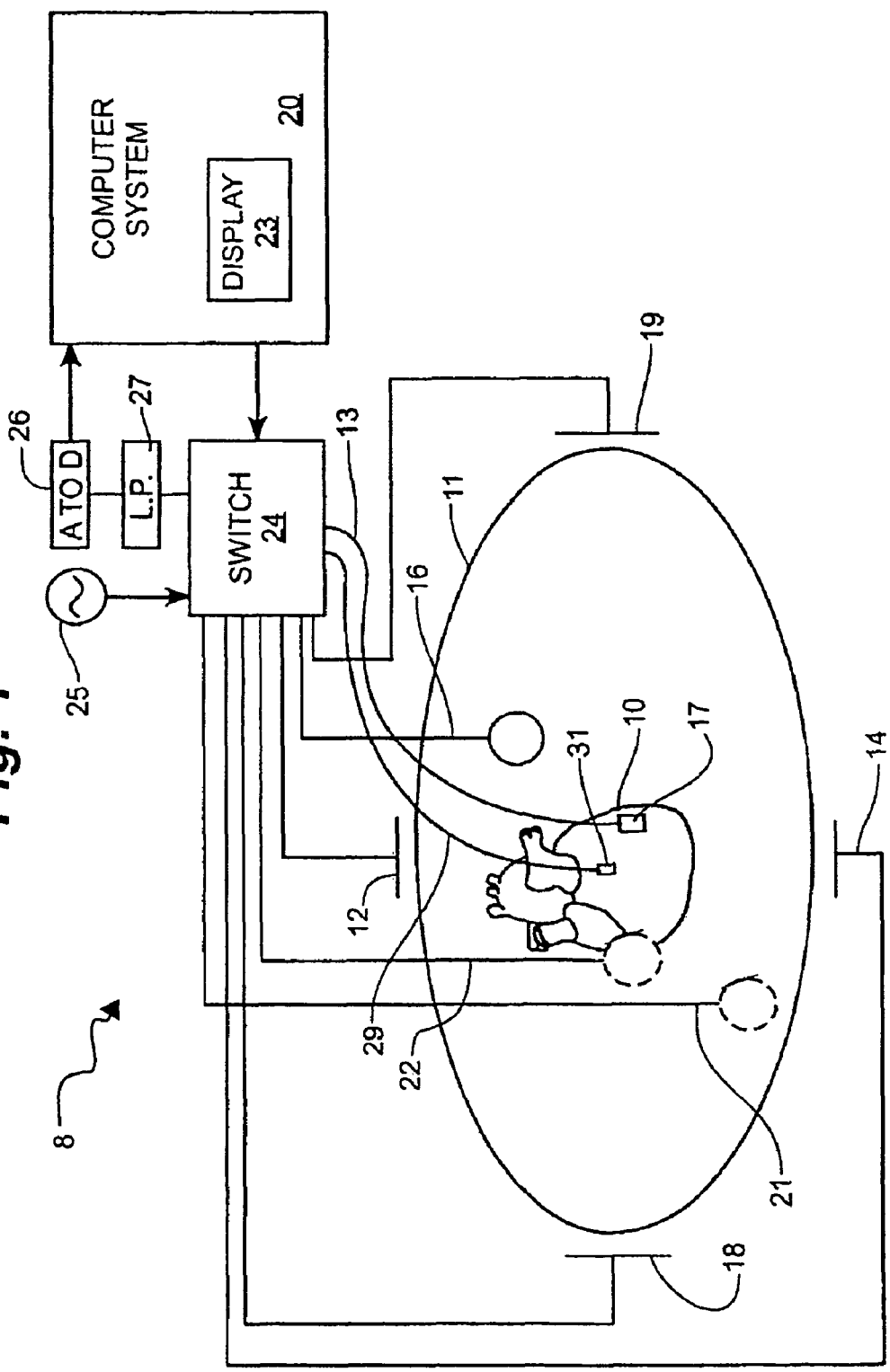
FIG. 1 is a schematic diagram of a system for performing a cardiac electrophysiology examination or ablation procedure wherein the location of one or more electrodes can be determined and recorded.

FIG. 1 is a schematic diagram of a system 8 according to the present invention for conducting cardiac electrophysiology studies by measuring electrical activity occurring in a heart 10 of a patient 11 and three-dimensionally mapping the electrical activity and/or information related to the electrical activity. In one embodiment, for example, the system 8 can instantaneously locate up to sixty-four electrodes in and/or around a heart and the vasculature of a patient, measure electrical activity at up to sixty-two of those sixty-four electrodes, and provide a three-dimensional map of time domain and/or frequency domain information from the measured electrical activity (e.g., electrograms) for a single beat of the heart 10. The number of electrodes capable of being simultaneously monitored is limited only by the number of electrode lead inputs into the system 8 and the processing speed of the system 8. The electrodes may be stationary or may be moving. In addition, the electrodes may be in direct contact with the wall of the heart, or may be merely generally adjacent to the wall of the heart, to collect the electrical activity. In another embodiment in which an array electrode is used, the system 8 can determine electrograms for up to about 3000 locations along the wall of the heart. Such an array electrode is described in detail in U.S. Pat. No. 5,662,108, which is hereby incorporated by reference herein in its entirety.

The patient 11 is depicted schematically as an oval for simplicity. Three sets of surface electrodes (e.g., patch electrodes) are shown applied to a surface of the patient 11 along an X-axis, a Y-axis, and a Z-axis. The X-axis surface electrodes 12, 14 are applied to the patient along a first axis, such as on the lateral sides of the thorax region of the patient (e.g., applied to the patient's skin underneath each arm) and may be referred to as the Left and Right electrodes. The Y-axis electrodes 18, 19 are applied to the patient along a second axis generally orthogonal to the X-axis, such as along the inner thigh and neck regions of the patient, and may be referred to as the Left Leg and Neck electrodes. The Z-axis electrodes 16, 22 are applied along a third axis generally orthogonal to the X-axis and the Y-axis, such as along the sternum and spine of the patient in the thorax region and may be referred to as the Chest and Back electrodes. The heart 10 lies between these pairs of surface electrodes. An additional surface reference electrode (e.g., a "belly patch") 21 provides a reference and/or ground electrode for the system 8. The belly patch electrode 21 is an alternative to a fixed intra-cardiac electrode 31. It should also be appreciated that in addition, the patient 11 will have most or all of the conventional electrocardiogram (ECG) system leads in place. This ECG information is available to the system 8 although not illustrated in the FIG. 1.

A representative catheter 13 having at least a single electrode 17 (e.g., a distal electrode) is also shown. This representative catheter electrode 17 is referred to as the "roving electrode" or "measurement electrode" throughout the specification. Typically, multiple electrodes on the catheter will be used. In one embodiment, for example, the system 8 may comprise up to sixty-four electrodes on up to twelve catheters disposed within the heart and/or vasculature of the patient. Of course, this embodiment is merely exemplary, and any number of electrodes and catheters may be used within the scope of the present invention.

The fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrode 17. The fixed reference electrode 31 may be used in addition to or alternatively to, the surface reference electrode 21 described above. In many instances, a coronary sinus electrode or other fixed electrode in the heart 10 can be used as a reference for measuring voltages and displacements.

Each surface electrode is coupled to the multiplex switch 24, and the pairs of electrodes are selected by software running on a computer 20, which couples the electrodes to a signal generator 25. The computer 20, for example, may comprise a conventional general-purpose computer, a special-purpose computer, a distributed computer, or any other type of computer. The computer 20 may comprise one or more processors, such as a single central-processing unit, or a plurality of processing units, commonly referred to as a parallel processing environment.

The signal generator 25 excites a pair of electrodes, for example the Y-axis electrodes 18, 19, which generates an electric field in the body of the patient 11 and the heart 10. During the delivery of the current pulse, the remaining surface electrodes are referenced to the surface electrode 21, and the voltages induced on these remaining electrodes are filtered via a low pass filter (LPF) 27. The LPF 27 may, for example, comprise an anti-aliasing filter (e.g., a 300 Hz analog LPF). The output of the LPF 27 is then provided to an analog-to-digital (A/D) converter 26 that converts the analog signal to a digital data signal. Further low pass filtering of the digital data signal may be subsequently performed by software executed on the computer 20 to remove electronic noise and cardiac motion artifact. This filtering may, for example, comprise a user-selectable cutoff frequency used to reduce noise. In this manner, the user can customize the system to trade off signal noise against signal fidelity according to the user's individual preferences. In this fashion, the surface electrodes are divided into driven and non-driven electrode sets. A pair of surface electrodes (e.g., the X-axis electrodes 12, 14) are driven by the signal generator 25, and the remaining, non-driven surface electrodes and other reference electrodes, if any, (e.g., the Y-axis electrodes 18, 19, the Z-axis electrodes 16, 22, the surface reference electrode 21, and, if present, the fixed reference electrode 31) are used as references to synthesize the position of any intracardial electrodes.

Generally, three nominally orthogonal electric fields are generated by a series of driven and sensed electric dipoles in order to realize catheter navigation in a biological conductor. Alternately, these orthogonal fields can be decomposed and any pairs of surface electrodes can be driven as dipoles to provide effective electrode triangulation. Additionally, such nonorthogonal methodologies add to the flexibility of the system. For any desired axis, the potentials measured across an intra-cardiac electrode 17 resulting from a predetermined set of drive (source-sink) configurations are combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, e.g., the belly patch 21, while the unexcited electrodes measure voltage with respect to the ground reference. The measurement electrode 17 placed in the heart 10 is exposed to the field from a current pulse and its voltage is measured with respect to ground, e.g., with respect to the belly patch 21. In practice, the catheters within the heart may contain multiple electrodes, and each electrode potential may be measured. As previously noted, at least one electrode may be fixed to the interior surface of the heart to form a fixed reference electrode 31, which is also measured with respect to ground. Data sets from each of the surface electrodes, the internal electrodes, and the virtual references are all used to determine the location of the measurement electrode 17 or other electrodes within the heart 10.

All of the raw electrode voltage data is measured by the A/D converter 26 and stored by the computer 20 under the direction of software. This electrode excitation process occurs rapidly and sequentially as alternate sets of surface electrodes are selected and the remaining non-driven electrodes are used to measure voltages. This collection of voltage measurements is referred to herein as the "electrode data set." The software has access to each individual voltage measurement made at each electrode during each excitation of each pair of surface electrodes.

Figure 2:
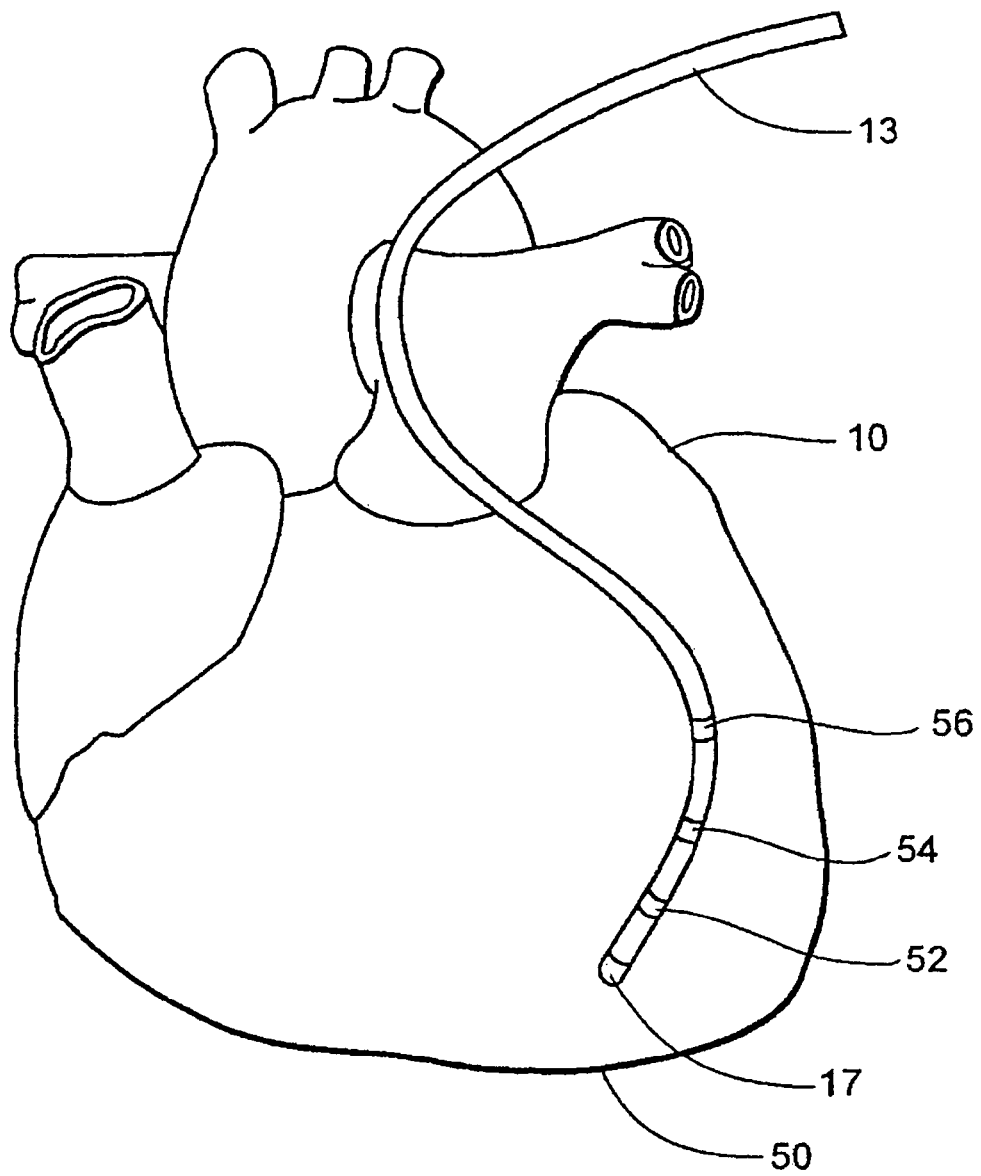
FIG. 2 is a schematic representation of a heart investigated by an electrophysiology catheter with several distal electrodes.

The raw electrode data is used to determine the "base" location in three-dimensional space (X, Y, Z) of the electrodes inside the heart, such as the roving electrode 17, and any number of other electrodes located in or around the heart and/or vasculature of the patient 11. FIG. 2 shows a catheter 13, which may be a conventional electrophysiology (EP) catheter, extending into the heart 10. In FIG. 2, the catheter 13 extends into the left ventricle 50 of the heart 10. The catheter 13 comprises the distal electrode 17 discussed above with respect to FIG. 1 and has additional electrodes 52, 54, and 56. Since each of these electrodes lies within the patient (e.g., in the left ventricle of the heart in this example), location data may be collected simultaneously for each of the electrodes. In addition, when the electrodes are disposed adjacent to the surface, although not necessarily directly on the surface of the heart, and when the signal source 25 is "off" (i.e., when none of the surface electrode pairs is energized), at least one of the electrodes 17, 52, 54, and 56 can be used to measure electrical activity (e.g., voltage) on the surface of the heart 10.

In summary, the system 8 first selects a set of electrodes and then drives them with current pulses. While the current pulses are being delivered, electrical activity, such as the voltages measured at least one of the remaining surface electrodes and in vivo electrodes are measured and stored. At this point, compensation for artifacts, such as respiration and/or impedance shifting may be performed as indicated above. As described above, various location data points are collected by the system 8 that are associated with multiple electrode locations (e.g., endocardial electrode locations). Each point in the set has coordinates in space. In one embodiment, the system 8 collects location data points for up to sixty-four electrodes that may be located on up to twelve catheters simultaneously or in close proximity to one another. However, smaller or larger data sets may be collected and result in less complex and lower resolution or more complex and higher resolution representations of the heart, respectively.

The electrode data may also be used to create a respiration compensation value used to improve the raw location data for the electrode locations as described in U.S. Patent Application Publication No. 2004/0254437, which is hereby incorporated herein by reference in its entirety. The electrode data may also be used to compensate for changes in the impedance of the body of the patient as described in co-pending U.S. patent application Ser. No. 11/227,580, filed contemporaneously with this application on 15 Sep. 2005, which is also incorporated herein by reference in its entirety.

The data used to determine the location of the electrode(s) within the heart are measured while the surface electrode pairs impress an electric field on the heart. A number of electrode locations may be collected by either sampling a number (e.g., sixty-two electrodes spread among up to twelve catheters) simultaneously or in sequence (e.g., multiplexed) and/or by sampling one or more electrodes (e.g., the roving electrode 17) being moved within the patient (e.g., a chamber of the heart). In one embodiment, the location data for individual electrodes are sampled simultaneously, which allows for collection of data at a single stage or phase of a heartbeat. In another embodiment, location data may be collected either synchronously with one or more phases of the heartbeat or without regard for any particular stage of the heartbeat. Where the data is collected across the phases of the heartbeat, data corresponding to locations along the wall of the heart will vary with time. In one variation, the data corresponding to the outer or inner locations may be used to determine the position of the heart wall at the maximum and minimum volumes, respectively. For example, by selecting the most exterior points it is possible to create a "shell" representing the shape of the heart at its greatest volume.

A three-dimensional model of a portion of the patient, e.g., a region of the patient's heart or surrounding vasculature, may be created from the location data points, e.g., during the same or a previous procedure, or a previously generated three-dimensional model, e.g., a segmented CT or MRI scan image, may be used. A segmented model indicates that a subregion of a three-dimensional image has been digitally separated from a larger three-dimensional image, e.g., an image of the right atrium separated from the rest of the heart. Exemplary segmentation applications include ANALYZE (Mayo, Minneapolis, Minn.), Verismo (St. Jude Medical, Inc., St. Paul, Minn.), and CardEP (General Electric Medical Systems, Milwaukee, Wis.). Where the three-dimensional model is created from the location data points collected by the system 8, for example, during a single procedure, the exterior-most location points in the data can be used to determine a shape corresponding to the volume of a region of the patient's heart.

In one variation, for example, a convex hull may be generated using standard algorithms such as the Qhull algorithm. The Qhull algorithm, for example, is described in Barber, C. B., Dobkin, D. P., and Huhdanpaa, H. T., "The Quickhull algorithm for convex hulls," *ACM Trans. on Mathematical Software,* 22(4):469-483, December 1996. Other algorithms used to compute a convex hull shape are known and may also be suitable for use in implementing the invention. This surface is then re-sampled over a more uniform grid and interpolated to give a reasonably smooth surface stored as a three-dimensional model for presentation to the physician during the same or a later procedure. Such a three-dimensional model, for example, provides an estimated boundary of the interior of the heart region from the set of points.

Figure 3:
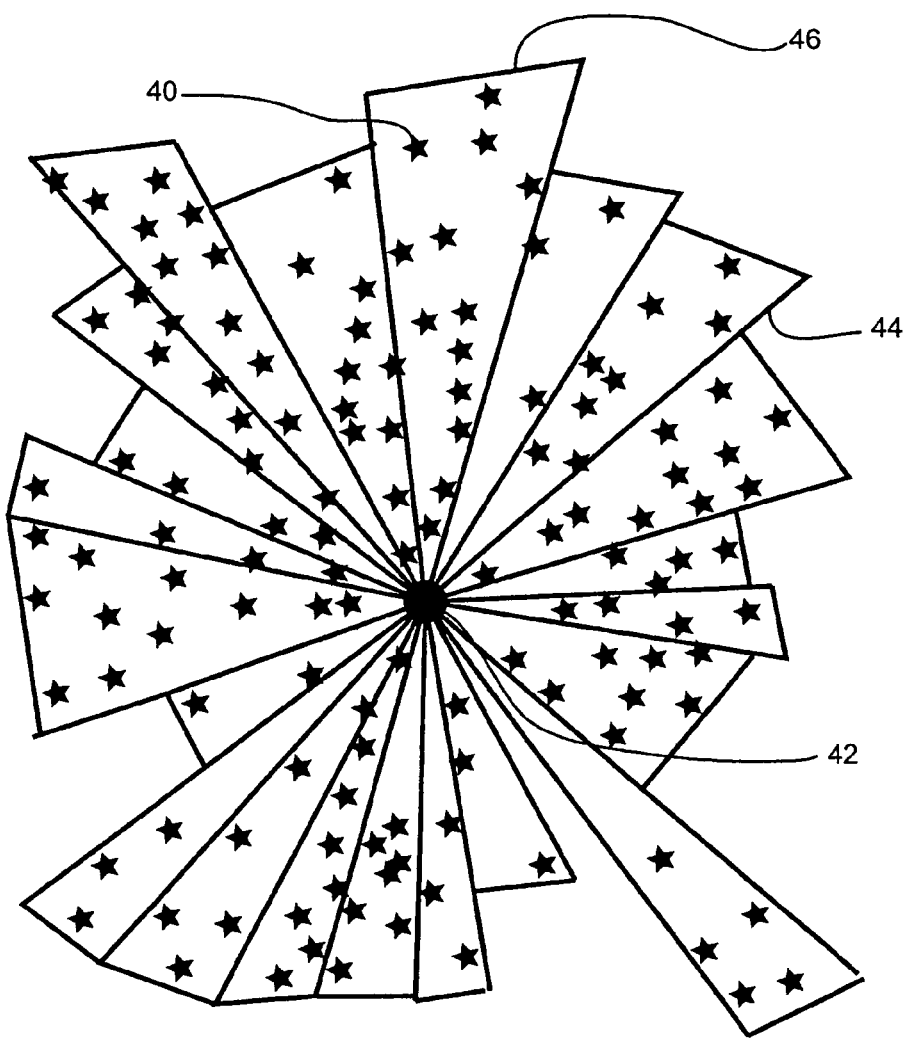
FIG. 3 is a schematic diagram of an exemplary methodology for rendering a surface of a heart cavity using recorded electrode position data points.

FIG. 3 schematically depicts another exemplary method for creating a shell corresponding to the shape of a heart chamber. The location data identifying position data points 40 of one or more electrodes within the heart chamber over a period of time is accessed. The location data may be represented as a cloud of points within the heart chamber. The most distant position data points 40 will thus correspond to the interior wall of the heart chamber in a relaxed or diastole state corresponding to its greatest volume. A shell or surface is rendered from this location data by fitting an array of "bins" 44 around groups of the position data points 40. The bins 44 are constructed by determining a mean center point 42 within the cloud of position data points 40 and then extending borders radially outward from the center point 42. The bins 44 extend to the furthest position data point 40 within the slice encompassed by the bin 44. It should be noted that even though FIG. 3 is schematically presented in two dimensions, the bins 44 are three-dimensional volumes. The radial end faces 46 of the bins 44 thus approximate the surface of the heart chamber wall. Common graphic shading algorithms can then be employed to "smooth" the surface of the shell thus created out of the radial end faces 46 of the bins 44.

Figure 4:
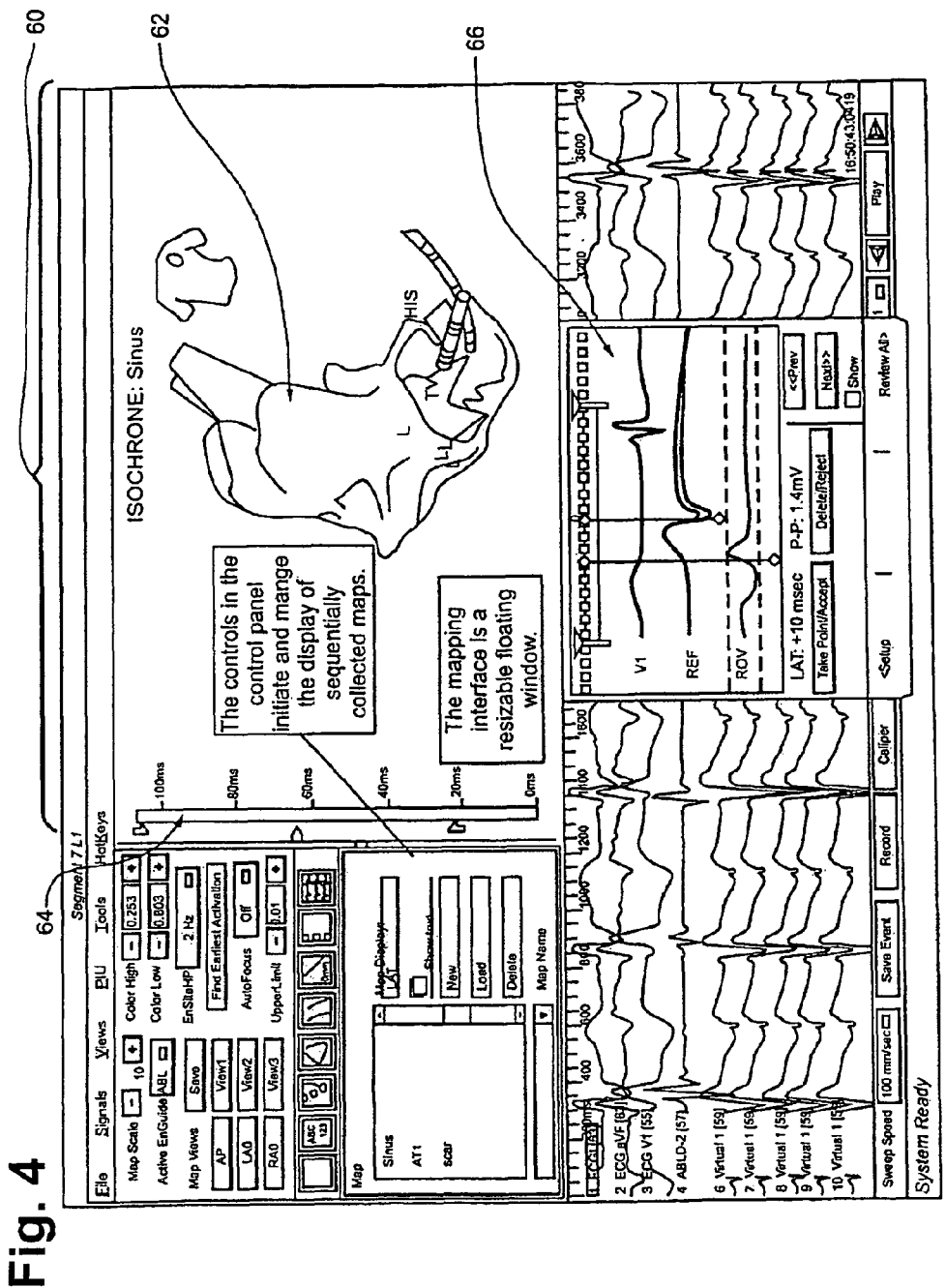
FIG. 4 is a schematic depiction of a graphical user interface for displaying electrocardiograph and related electrophysiological information to a clinician.

Various electrophysiology data may be measured and presented to a cardiologist through the display 23 of the system 8 shown in FIG. 1. FIG. 4 depicts an illustrative computer display that may be displayed via the computer 20. The display 23, for example, may be used to show data to a user, such as a physician, and to present certain options that allow the user to tailor the configuration of the system 8 for a particular use. It should be noted that the contents on the display can be easily modified and the specific data presented is illustrative only and not limiting of the invention. An image panel 60 shows a three-dimensional model of a heart chamber 62 identifying regions that received a depolarization waveform at the same time, i.e., "isochrones," mapped to the model in false color or grayscale. The isochrones are, in one variation, mapped to three-dimensional coordinates (e.g., X, Y, Z) corresponding to the electrogram from which they were obtained. The isochrones are also shown in guide bar 64 as a key, identifying information associated with a particular color or grayscale mapped to the three-dimensional model. In this image, the locations of multiple electrodes on a pair of catheters are also mapped to the three-dimensional model. Other data that may be mapped to the heart surface model include, for example, the magnitude of a measured voltage and the timing relationship of a signal with respect to heartbeat events. Further, the peak-to-peak voltage measured at a particular location on the heart wall may be mapped to show areas of diminished conductivity and may reflect an infarct region of the heart.

Figure 5:
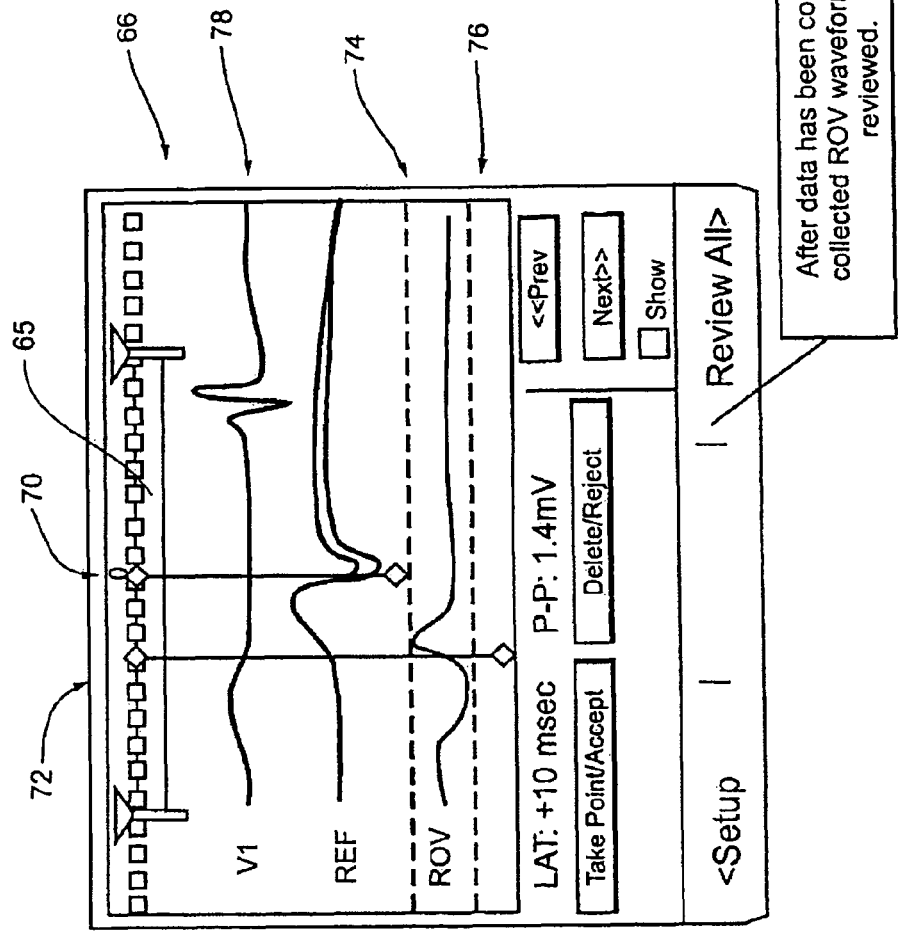
FIG. 5 is an enlargement of the panel 66 depicted in FIG. 4.

In the variation shown in FIG. 4, for example, the guide bar 64 is graduated in milliseconds and shows the assignment of each color or grayscale to a particular time relationship mapped to the three-dimensional model. The relationship between the color or grayscale on the three-dimensional model image 62 and the guide bar 64 can also be determined by a user with reference to the information shown in panel 66. FIG. 5 shows an enlargement of the panel 66 depicted in FIG. 4. The panel 66, in this variation, shows timing information used to generate isochrones mapped on the three-dimensional model 62 shown in FIG. 4. In general, a fiducial point is selected as the "zero" time. In FIG. 5, for example, the inflection point 70 of a voltage appearing on a reference electrode is used as the primary timing point for the creation of isochrones. This voltage may be acquired from either a virtual reference or a physical reference (e.g., the roving electrode 31 shown in FIG. 1). In this variation, the voltage tracing corresponding to the fiducial point is labeled "REF" in FIG. 5. The roving electrode signal is depicted in FIG. 5 and is labeled "ROV." The inflection point 72 of the voltage signal ROV corresponds to the roving electrode 31. The color guide bar 65 shows the assignment of color or grayscale tone for the timing relationship seen between inflection points 70 and 72 of the reference and roving voltage signals REF and ROV, respectively.

The amplitude of the voltage signal ROV corresponding to the roving electrode 31 is also shown on panel 66 of FIG. 5. The amplitude of the time-varying signal ROV is located between two adjustable bands 74 and 76, which can be used to set selection criteria for the peak-to-peak voltage of the signal ROV. In practice, regions of the heart with low peakto-peak voltage are the result of infarct tissue, and the ability to convert the peak-to-peak voltage to grayscale or false color allows identification of the regions that are infarct or ischemic. In addition, a time-varying signal 78 "V1" is also shown and corresponds to a surface reference electrode, such as a conventional ECG surface electrode. The signal 78 V1, for example, may orient a user, such as a physician, to the same events detected on the surface of the patient.

As described above, the electrodes of at least one EP catheter are moved over the surface of the heart and while in motion they detect the electrical activation of the heart or other EP signals on the surface of the heart. During each measurement, the real-time location of the catheter electrode is noted along with the value of the EP voltage or signal. This data is then projected onto a surface of the three-dimensional model corresponding to the location of the electrode when the sampled EP data was taken. Since this data is not taken while the locating surface electrodes are energized, a projection process may be used to place the electrical information on the nearest heart surfaces represented by the geometry. In one exemplary embodiment, for example, two close points or locations in the EP data set are selected, and the data is mapped to a point determined to be the closer of the two points (e.g., via "dropping" a line to the "nearest" surface point on the geometric surface). This new point is used as the "location" for the presentation of EP data in the images presented to the physician.

Various time-domain information related to the EP activity in and/or around the heart of a patient may be mapped to the three-dimensional model. For example, the time difference of an action potential measured at a roving electrode and a reference electrode, the peak-to-peak voltage of an action potential measured at the roving electrode, and/or the peak negative voltage of an action potential measured at the roving electrode may be mapped to a three-dimensional model. In one embodiment, EP activity from up to sixty-two roving electrodes may be collected and mapped to the three-dimensional model.

Figure 6:
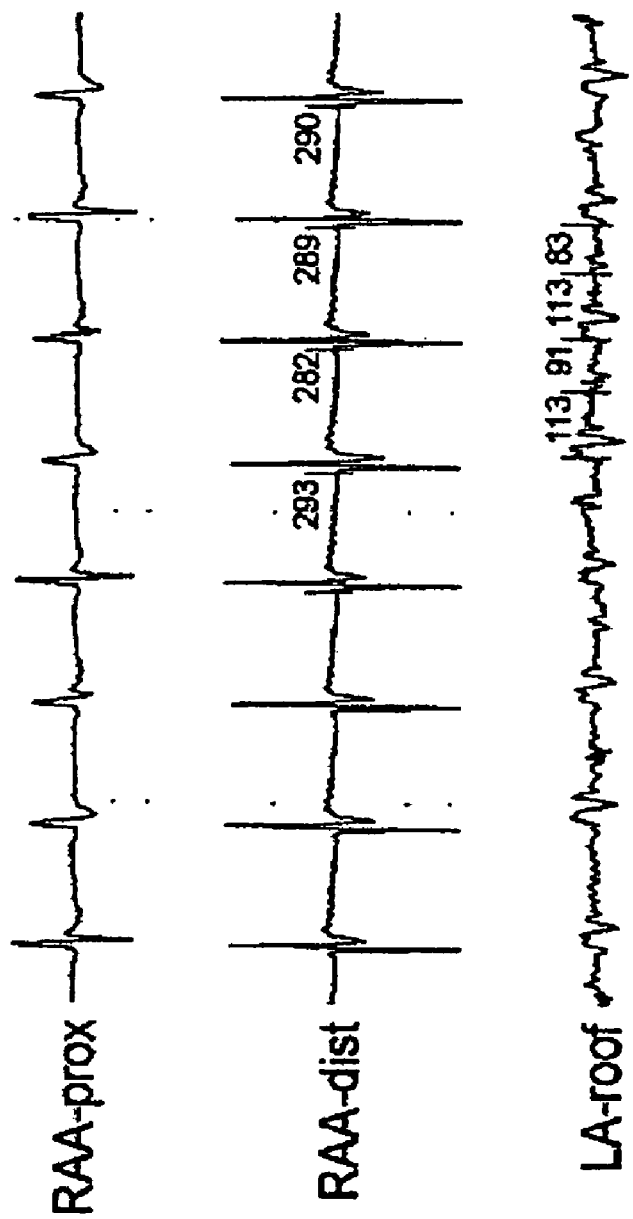
FIG. 6 shows side-by-side views of time-varying electrograms collected for various locations along a wall of a heart.
Figure 7:
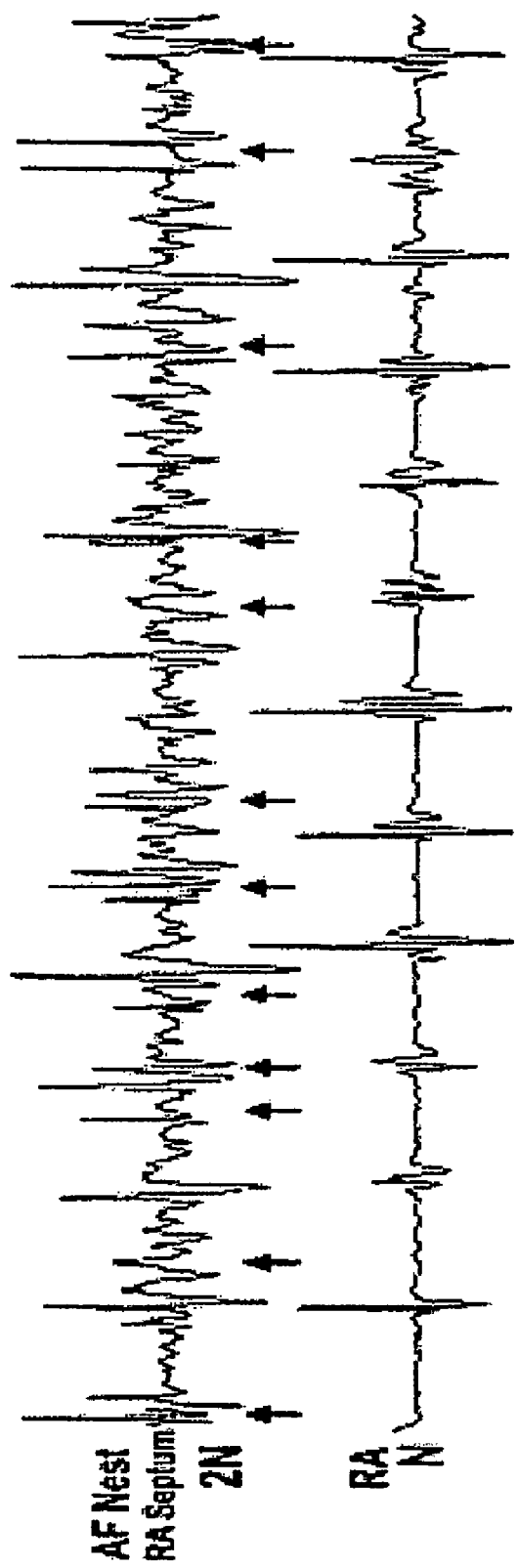
FIG. 7 shows side-by-side views of time-varying electrograms collected for various locations along a wall of a heart.

Complex fractionated electrogram (CFE) and frequency-domain information may also be mapped to the three-dimensional model. CFE information, for example, may be useful to identify and guide ablation targets for atrial fibrillation. CFE information refers to irregular electrical activation (e.g., atrial fibrillation) in which an electrogram comprises at least two discrete deflections and/or perturbation of the baseline of the electrogram with continuous deflection of a prolonged activation complex (e.g., over a 10 second period). Electrograms having very fast and successive activations are, for example, consistent with myocardium having short refractory periods and micro-reentry. FIG. 6, for example, shows a series of electrograms. The first two electrograms, RAA-prox and RAA-dist, comprise typical electrograms from the right atrium of a patient such as from a proximal roving electrode and a distal roving electrode in the right atrium of a patient, respectively. The third electrogram, LA-roof, comprises a CFE, such as from the roof of the patient's left atrium. In this third electrogram, LA-roof, the cycle lengths indicated by the numbers shown in the electrogram are substantially shorter than the cycle lengths indicated by the numbers shown in the first two electrograms, RAA-prox and RAA-dist. In another example shown in FIG. 7, a first electrogram RA-Septum comprises fast and successive activations indicated by the arrows compared to the second electrogram RA. The fast and successive activations, for example, can be consistent with myocardial tissue having short refractory periods and micro-reentry, e.g., an atrial fibrillation "nest."

The presence of CFE information can be detected from the EP information (e.g., electrograms) collected by an electrode, for example, by monitoring the number of deflections within an electrogram segment; calculating the average time between deflections within an electrogram segment; monitoring the variation of time between deflections within a cycle length of an electrogram; and calculating slopes, derivatives, and amplitudes of electrograms. For example, discrete activations have an associated peak-to-peak value measured over a specified time period. This peak-to-peak value may be used to quantify a discrete activation. As shown in FIG. 5, a time instant of the discrete activations can be marked on the electrogram on the user display. The time instant and/or other quantifications of the fractionation of the electrogram may be used to determine the presence and/or absence of CFE information. The mean interval between discrete activations within a predetermined time period may, for example, be used as an index to quantify the degree of fractionation of a given electrogram. In this example, a value of one may be assigned to the electrogram if there is only one discrete activation within the given time period, and a lesser or higher value may be assigned if more than one discrete activation is present in the given time period. Another quantification may comprise, for example, quantifying the variance in time between discrete activations of an electrogram. These or other quantifications of the time-domain correlate with the morphology of the electrogram and are, in turn, based upon the underlying physiology of the region for which the electrogram was sampled.

Preferably, the mean interval between discrete activations within a predetermined time period may be calculated for a plurality of locations within the heart, so that comparisons may be made from one location on the heart to another. This may be accomplished using a plurality of electrodes, or by using the same electrodes repositioned at a plurality of locations. Software may be used to display mean interval information as a function of location on the heart, for example, by assigning colors to various measured values. Such software provides the user of the system with a visual tool to help identify potential problem areas.

In a preferred embodiment, a standard deviation calculation is desired for the CFE information. It has been discovered that standard deviation calculations for CFE information provide a useful metric for determining the presence and/or absence of CFE information, and accordingly, is a useful metric for identifying areas that may need ablating. The presence of CFE information can be detected from the EP information (e.g., electrograms) collected by an electrode, for example, by monitoring the number of deflections within an electrogram segment and calculating the standard deviation of the time intervals between discrete activations within an electrogram segment. As discussed above in connection with FIG. 5, the occurrence of the discrete activations can be marked on the electrogram on the user display. It is also possible to utilize software to analyze and identify the occurrences of discrete activations, which information may then be evaluated for standard deviations. Standard deviations measurements may be calculated using known algorithms on sections of data for time periods of less than 1 second or for much longer time periods of several seconds, such as 20-60 seconds. Preferably, the time period ranges from about 1 second to about 10 seconds, and more preferably for time periods ranging from about 3 seconds to about 8 seconds. In one embodiment, the user may specify the window for analysis. Preferably, standard deviation determinations are made for multiple locations within a portion of the heart, so that comparisons may be made from one location on the heart to another. This may be accomplished using a plurality of electrodes, or by using the same electrodes repositioned at a plurality of locations. Software may be used to display standard deviation information as a function of location on the heart, for example, by assigning colors to various measured values. Such software provides the user of the system with a visual tool to help identify potential problem areas. When the standard deviation exceeds a particular threshold, this may indicate a high degree of fractionation in the electrogram.

In yet another preferred embodiment, the CFE information is presented using both mean interval data and standard deviation of the intervals. Preferably, the mean and standard deviation information for intervals between discrete activations within a predetermined time period are calculated for a plurality of locations within the heart, so that comparisons may be made from one location on the heart to another. Software may be used to display mean and standard deviation information as a function of location on the heart, for example, by assigning colors to various measured values. This may take the form of two separate images that may be compared to each other—or a single image in which the two sets of data are superimposed upon the same three-dimensional model. Another way to display the combined information is to mathematically relate the two metrics, for example, the standard deviation divided by the mean, or the mean divided by the standard deviation, and then display the result on a single image, again assigning colors to various calculated values. Such presentation software provides the user of the system with a visual tool to help identify potential problem areas using both mean and standard deviation information. A physician, for example, may find it of significance that a particular location has a high standard deviation and a low mean. A goal of this invention is to provide tools to help a physician analyze the situation using as much useful information as possible.

In diagnosing atrial fibrillation and guiding an ablation catheter, the electrograms corresponding to physiological mechanisms for initiating and sustaining atrial fibrillation may be identified by quantifying the fractionation of the electrograms. These quantifications, in turn, may be used to identify regions to be ablated to eliminate the atrial fibrillation. Mid-diastolic potentials within an ischemic area of the cardiac chamber may also be identified by quantifying the fractionation of the electrograms collected in a region of the heart. Healthy tissue would correspond to non-fractionated electrograms (i.e., a single discrete activation), while unhealthy tissue (e.g., ischemic tissue) would correspond to fractionated electrograms (i.e., multiple discrete activations and/or perturbations of the baseline). The time instant or other quantifications of CFE information in electrograms may then be mapped to a three-dimensional model as described above.

In addition to and/or alternatively to the time-domain information analyzed and mapped from the collected EP information, frequency-domain information may also be mapped to a three-dimensional model. In one embodiment, for example, a fast Fourier transform (FFT) or other method of translating a time-varying signal into frequency-domain information may be used to translate the collected signal into a frequency-domain. The frequency-domain depicts a spectrum that represents the energy or power of frequency components of a time-varying electrogram signal. FFTs and other transforms are known in the art and are not discussed in further detail herein.

FIG. 8 shows a side-by-side comparison of compact myocardial muscle and fibrillar myocardial muscle that together form the wall of the heart. Compact myocardial muscle tissue comprises groups of tightly-connected cells that conduct electrical activity during depolarization of the heart in a homogenous fashion by transmitting electrical activity at equal speeds in any direction. Fibrillar myocardial muscle tissue, however, typically comprises loosely connected cells, such as transitions between neural, vascular, and atrial tissue. Fibrillar myocardial muscle tissue may also be formed by stretching and/or degeneration of cells leading to poor connections between such damaged tissue. In row A, the first column shows the homogenous or uniform activation of compact myocardial muscle tissue during depolarization of the heart wall. In the second column, however, the irregular activation of fibrillar myocardial muscle tissue is shown during depolarization in which a wave travels at different rates through different strands or portions of the fibrillar myocardial muscle tissue, thus causing asynchronous contraction in different portions of the myocardium.

In row B, time-domain electrogram signals are shown for the compact myocardial muscle tissue and the fibrillar myocardial muscle tissue during a depolarization phase of a heartbeat. As shown in FIG. 8, the time-domain electrogram signals typically comprise a biphasic or triphasic shape for compact myocardial muscle tissue (shown in column 1) and a more polyphasic shape for fibrillar myocardial muscle tissue (shown in column 2). Finally, the frequency-domain of the electrogram signals of row B for compact myocardial muscle tissue and fibrillar myocardial muscle tissue is shown in row C. The frequency-domain is obtained by performing an FFT on a time period of the time-varying electrograms shown row B, column 1 for compact myocardial muscle tissue and row B, column 2 for fibrillar myocardial muscle tissue. As shown in row C of FIG. 8, the frequency-domain for compact myocardial muscle tissue typically comprises a higher amplitude at a single peak located around a fundamental frequency, while the frequency-domain for the fibrillar myocardial muscle tissue typically comprises a lower amplitude at its fundamental frequency due to a right-shift of the frequency caused by a number of harmonic frequency components.

As shown in FIG. 8, fibrillar myocardial muscle tissue can lead to irregular wavefronts of electrical activity during depolarization of the heart. The greater the ratio of fibrillar myocardial muscle tissue to compact myocardial muscle tissue, the more likely there is a propensity for atrial fibrillation. In such areas "atrial fibrillation nests" (or "AFIB nests") may be identified as potential sources of atrial fibrillation. Thus, by use of frequency-domain information, a physician may be able to further identify potential trouble spots that may lead to atrial fibrillation.

Figure 9A:
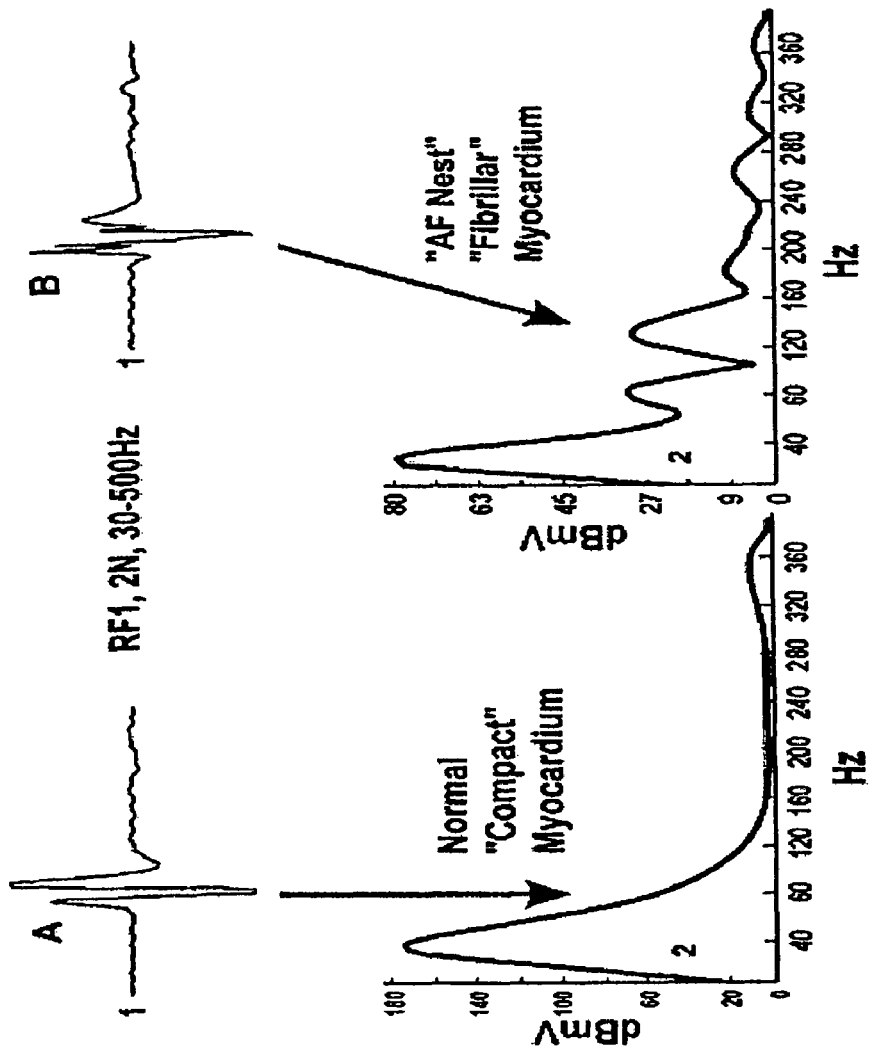
FIG. 9A shows a side-by-side comparison of time-domain and frequency-domain information for electrograms.

Various numerical indices can be obtained from the frequency-domain of the electrogram signal. Any of these indices can then be mapped to a three-dimensional model of a patient's heart to allow a user such as a physician to identify locations on the wall of the heart that correspond to a particular characteristic. In one exemplary variation of the present invention, a dominant frequency of an electrogram signal can be identified in the frequency-domain, which has been obtained via an FFT. As can be seen in FIG. 9A, for example, a typical normal, or compact, myocardial muscle tissue may have a single peak in the spectrum, while a fibrillar myocardial muscle tissue has more spectral peaks than does a compact myocardial muscle tissue. The number of spectral peaks may be determined for multiple points around the wall of the heart on a three-dimensional model as described above.

In another variation of the present invention, a maximum peak amplitude at the dominant frequency may be determined from the frequency-domain of the electrogram signal and may be mapped to a three-dimensional model of the heart. In FIG. 9A, for example, the maximum peak amplitude at the dominant frequency of compact myocardial muscle tissue can be seen to be higher at about 175 dB mV, while the maximum peak amplitude at the dominant frequency of fibrillar myocardial muscle tissue is lower at about 80 dB mV. These values may also be mapped onto a three-dimensional model of the heart.

Figure 9B:
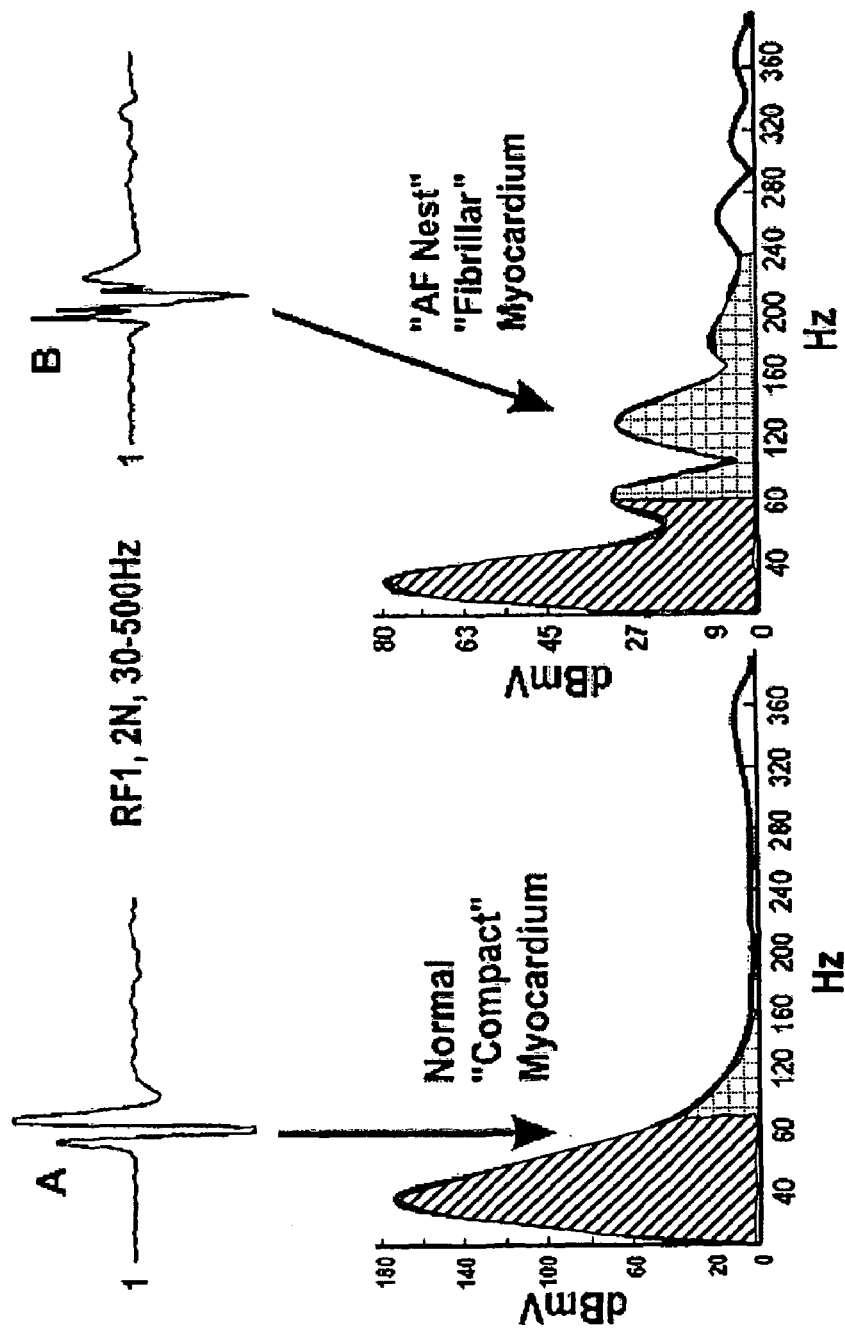
FIG. 9B shows a side-by-side comparison of time-domain and frequency-domain information for electrograms with energy in multiple spectral bands shown in cross-hatch.

In yet another variation, a ratio of energy in one band of the frequency-domain to the energy in a second band of the frequency-domain may be determined and mapped to a three-dimensional model of the heart. For example, FIG. 9B shows the ratio of energy in the passband of 60 to 240 Hz to the energy below 60 Hz is higher for the spectrum of electrograms from fibrillar myocardial muscle tissue than in the spectrum of electrograms from compact myocardial muscle tissue.

While examples of time-domain and frequency-domain information have been described herein as able to be translated to a three-dimensional map of a patient's heart, one skilled in the art would recognize that other time- and frequency-domain information may also be determined and mapped to a three-dimensional model. For example, the following information may be determined from the time-domain or frequency-domain and mapped to a three-dimensional model: a low-frequency or high-frequency passband of interest (e.g., in Hz); a frequency with the maximum energy in a passband (e.g., in Hz); a number of peaks within a passband (e.g., a count); an energy, power, and/or area in each peak (e.g., dB); a ratio of energy and/or area in each peak to that in another passband; and a width of each peak in a spectra (e.g., in Hz).

Figure 10:
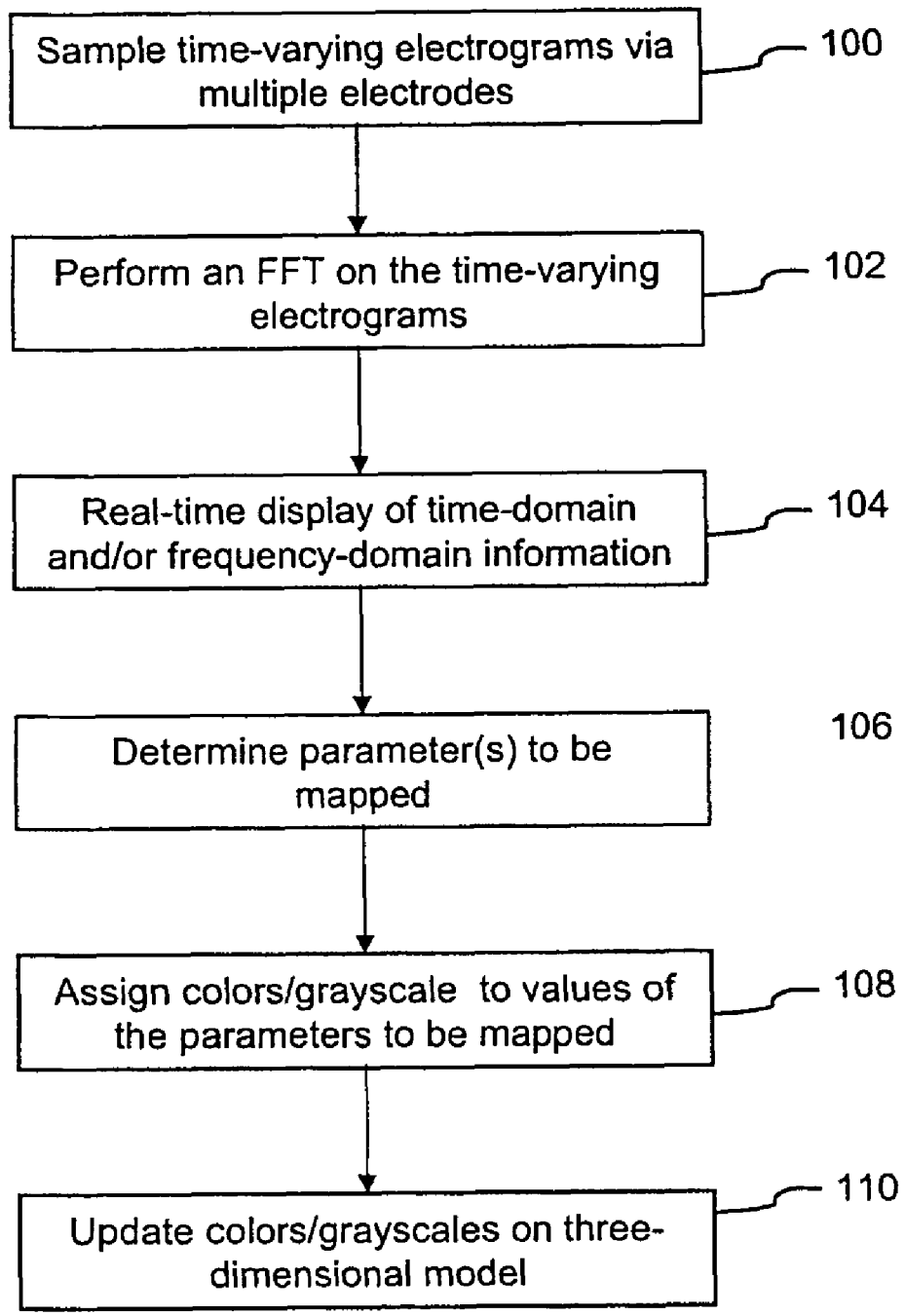
FIG. 10 shows a method for collecting electrograms and mapping time-domain and/or frequency-domain electrogram information on a three-dimensional model.

FIG. 10 shows one example of a method for determining information from a time-varying electrogram in the time-domain and/or frequency-domain and mapping that information onto a three-dimensional model (e.g., a heart). In operation 100, a number of electrodes (e.g., contact or non-contact, unipolar or bipolar mapping electrodes) are used to sample a time-varying electrogram signal. The electrogram signal, for example, may be sampled for multiple sites along the wall of the heart and/or the surrounding vasculature.

An FFT is then performed over a time period of the time-varying electrogram to determine frequency-domain information for that electrogram in operation 102. A real-time display of the time-domain and/or frequency-domain information may be displayed in operation 104. One or more parameters are then determined in operation 106. Exemplary parameters are described above and include, for example, a time difference between a roving electrode and a reference electrode; the peak-to-peak voltage of the roving electrode; the peak negative voltage of the roving electrode; CFE information; a dominant frequency of an electrogram signal; a maximum peak amplitude at the dominant frequency; a ratio of energy in one band of the frequency-domain to the energy in a second band of the frequency-domain; a low-frequency or high-frequency passband of interest; a frequency with the maximum energy in a passband; a number of peaks within a passband; an energy, power, and/or area in each peak; a ratio of energy and/or area in each peak to that in another passband; and a width of each peak in a spectrum. Colors, shades of colors, and/or grayscales are assigned to values of the parameters to be identified in operation 108, and colors, shades of colors, and/or grayscales corresponding to the parameters for the electrograms sampled by the electrodes are updated on a three-dimensional model (e.g., of a heart) continuously and in real time in operation 110.

One particular area of interest is the mapping of areas of the heart comprised of autonomic nerve cells. ECG information may be mapped to identify the foci of electrical propagation through the heart. The initiation points for electrical signals will generally be autonomic cell bundles, or ganglia plexi. To the extent that any arrhythmia is caused by a malfunction in autonomic cells, the ability to detect this malfunction can significantly aid in the efficacy of treatment and minimize the scope of treatment. A particular advantage to mapping the complex fractionated electrograms in the frequency domain is the ability to quickly identify and locate such areas of arrhythmia. For example, if it is determined that a specific autonomic bundle is the source of fibrillation, targeting this area of initial neural input instead of treating multiple areas of fibrillar tissue can substantially reduce the number of lesions required to treat the condition.

Although multiple embodiments of this invention have been described above with a certain degree of particularity, those skilled in the art could make numerous alterations to the disclosed embodiments without departing from the spirit or scope of this invention. For example, while the description above describes data being mapped to a three-dimensional model, data may be mapped to any map including, but not limited to, a two- or three-dimensional, static or time-varying image or model.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A system for presenting information representative of electrophysiological activity of a patient, the system comprising:

at least one electrode adapted to receive at least one stream of electrical data from at least one location within a heart of a patient, said data comprising complex fractionated electrogram information;

at least one processor coupled to the at least one electrode to receive the at least one stream of electrical data from at least one location and to determine the measurement location of the electrode within the heart of the patient while it is receiving the stream of electrical data, said at least one processor associating the measurement location with the at least one stream of electrical data being received;

at least one memory to store the measurement location of the electrode and the at least one stream of electrical data being received;

software to analyze the at least one stream of electrical data to identify occurrences of discrete electrical activations within a predetermined window, and to quantify the complex fractionated electrogram information contained in the predetermined window based upon a variance in time between discrete activations of an electrogram within the predetermined window; and a presentation device to present said quantified complex fractionated electrogram information and its respective measurement location on a model of the heart of the patient.

2. The system of claim 1, wherein the presentation device presents the variance information on the model of the heart at a location that corresponds to a point at which the electrical data was measured.

3. The system of claim 2, wherein the software also quantifies the complex fractionated electrogram information contained in the predetermined window based upon a mean interval between discrete activations within the predetermined window, and the presentation device also presents the mean interval information on the model of the heart at a location that corresponds to a point at which the electrical data was measured.

4. The system of claim 1, wherein the software also quantifies the complex fractionated electrogram information contained in the predetermined window based upon a mean interval between discrete activations within the predetermined window, and the presentation device presents the mean interval information on the model of the heart at a location that corresponds to a point at which the electrical data was measured.

5. The system of claim 1, wherein the at least one electrode comprises a plurality of electrodes adapted to receive electrical data simultaneously from a plurality of locations within the patient;

wherein the processor receives a plurality of streams of electrical data from the plurality of electrodes, determines the measurement locations of each of the plurality of electrodes, and associates each measurement location with the stream of electrical data that is measured at the respective measurement location;

wherein the software analyzes each of the plurality of streams of data to identify occurrences of discrete electrical activations within a predetermined window, and quantifies the complex fractionated electrogram information contained in each predetermined window of the plurality of streams of data; and wherein the presentation device presents the quantified complex fractionated electrogram information for each of a plurality of streams of data at a plurality of locations, wherein each of the plurality of locations corresponds to a location in the heart at which the underlying electrical data was measured.

6. The system of claim 1, wherein the presentation device presents the quantified complex fractionated electrogram information by assigning at least one color, shade of color, or grayscale to represent the complex fractionated electrogram information on a model of the heart.

7. A method of analyzing and presenting information representative of electrophysiological activity of a patient, comprising the steps of:

obtaining a cardiac electrophysiology map comprising position information identifying a plurality of measurement locations and electrophysiology measurements made at each of the plurality of measurement locations, said electrophysiology measurements comprising at least one stream of complex fractionated electrogram information;

processing the at least one stream of complex fractioned electrogram information measured at one of the plurality of measurement locations to identify occurrences of discrete electrical activations within a predetermined window, and to quantify the complex fractionated electrogram information contained in the predetermined window based upon a variance in time between discrete activations of an electrogram within the predetermined window; and presenting the quantified complex fractionated electrogram information and its respective measurement location on a model of the heart of the patient.

8. The method of claim 7, wherein the presenting step further comprises presenting the variance information on the model of the heart at a location that corresponds to a point where the electrical data was measured.

9. The method of claim 8, wherein the processing step further comprises quantifying the complex fractionated electrogram information contained in the predetermined window based upon a mean interval between discrete activations within the predetermined window; and the presenting step further comprises presenting the mean interval information on the model of the heart at a location that corresponds to a point at which the electrical data was measured.

10. The method of claim 7, wherein the processing step further comprises quantifying the complex fractionated electrogram information contained in the predetermined window based upon a mean interval between discrete activations within the predetermined window; and the presenting step further comprises presenting the mean interval information on the model of the heart at a location that corresponds to a point where the electrical data was measured.

11. The method of claim 7, wherein the step of obtaining a cardiac electrophysiology map further comprises:

using a plurality of electrodes to receive electrical data simultaneously from a plurality of measurement locations within the patient; and obtaining a cardiac electrophysiology map comprising position information identifying a plurality of measurement locations and electrophysiology measurements made at each of the plurality of measurement locations, said electrophysiology measurements comprising at least one stream of complex fractionated electrogram information;

wherein the step of processing the stream of complex fractioned electrogram information further comprises processing each of the plurality of streams of data to identify occurrences of discrete electrical activations within a predetermined window, and quantifying the complex fractionated electrogram information contained in each predetermined window of the plurality of streams of data; and wherein the step of presenting the quantified complex fractionated electrogram information further comprises presenting the quantified complex fractionated electrogram information for each of a plurality of streams of data at a plurality of locations, wherein each of the plurality of locations corresponds to a location in the heart at which the underlying electrical data was measured.

12. The method of claim 7, wherein the presenting step further comprises presenting the quantified complex fractionated electrogram information by assigning at least one color, shade of color, or grayscale to represent the complex fractionated electrogram information on a model of the heart.

13. A method of analyzing and presenting information representative of electrophysiological activity of a patient, comprising the steps of:

obtaining a cardiac electrophysiology map comprising position information identifying a measurement location and electrophysiology measurements made at the measurement locations, said electrophysiology measurements comprising at least one stream of complex fractionated electrogram information;

processing the at least one stream of complex fractioned electrogram information measured at the measurement locations to identify occurrences of discrete electrical activations within a predetermined window, and to quantify the standard deviation of the time intervals between occurrences of discrete electrical activations within the predetermined window; and presenting the standard deviation information on the model of the heart at a location that corresponds to a point where the at least one stream of complex fractioned electrogram information was measured.

* * * * *